United States Patent
McMichael et al.

(10) Patent No.: US 6,907,992 B2
(45) Date of Patent: Jun. 21, 2005

(54) SURGICAL KIT FOR "PUSH" TYPE PERCUTANEOUS ENDOSCOPIC GASTROSTOMY PROCEDURES

(75) Inventors: Donald J. McMichael, South Jordan, UT (US); Mark E. Foster, Sandy, UT (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 233 days.

(21) Appl. No.: 10/085,417

(22) Filed: Feb. 28, 2002

(65) Prior Publication Data

US 2003/0159966 A1 Aug. 28, 2003

(51) Int. Cl.⁷ .............................................. B65D 69/00
(52) U.S. Cl. ...................... 206/571; 206/370; 206/562; 206/570; 220/527
(58) Field of Search ................................ 206/363–370, 206/438, 439, 440, 570–572, 562–564; 220/527–528

(56) References Cited

U.S. PATENT DOCUMENTS

| | | | |
|---|---|---|---|
| 4,085,845 A | | 4/1978 | Perfect |
| 4,170,300 A | | 10/1979 | Pick |
| 4,293,074 A | * | 10/1981 | Dunsky ...................... 206/572 |
| D277,508 S | | 2/1985 | Clair |
| 4,522,302 A | * | 6/1985 | Paikoff ....................... 206/570 |
| 4,523,679 A | | 6/1985 | Paikoff et al. |
| D281,704 S | | 12/1985 | Deacon |
| D282,279 S | | 1/1986 | Holewinski et al. |
| D282,280 S | | 1/1986 | Holewinski et al. |
| 4,573,576 A | | 3/1986 | Krol |
| 4,595,102 A | | 6/1986 | Cianci et al. |
| D288,481 S | | 2/1987 | Holewinski et al. |

(Continued)

FOREIGN PATENT DOCUMENTS

| | | |
|---|---|---|
| EP | 0407663 B1 | 1/1991 |
| WO | 9508302 | 3/1995 |
| WO | 9607364 | 4/1996 |
| WO | 0057810 | 10/2000 |

OTHER PUBLICATIONS

U.S. Appl. No. 10/085,637, filed Feb. 28, 2002.
U.S. Appl. No. 10/085,639, filed Feb. 28, 2002.
U.S. Appl. No. 10/085,630, filed Feb. 28, 2002.
Patent Abstract of Japan No. 10229964, Sep. 2, 1998.

*Primary Examiner*—Luan K. Bui
(74) *Attorney, Agent, or Firm*—Dority & Manning, P.A.

(57) ABSTRACT

A surgical kit is provided for a "push" percutaneous endoscopic gastrostomy (PEG) procedure. The kit includes offset planar surfaces and at least one article recess defined in the planar surfaces. The recesses are adapted to hold at least one article used in performing a "push" PEG procedure.

21 Claims, 7 Drawing Sheets

U.S. PATENT DOCUMENTS

| | | |
|---|---|---|
| D288,606 S | 3/1987 | Blatherwick et al. |
| 4,739,883 A | 4/1988 | Mohs et al. |
| 4,828,113 A | 5/1989 | Friedland et al. |
| 4,886,165 A | 12/1989 | Annett |
| 4,928,830 A | 5/1990 | Brewer |
| 5,011,020 A | 4/1991 | Stevens et al. |
| 5,031,768 A | 7/1991 | Fischer |
| 5,031,775 A | 7/1991 | Kane |
| 5,058,580 A | 10/1991 | Hazard |
| 5,098,391 A * | 3/1992 | Pantages et al. ............ 206/571 |
| 5,112,310 A | 5/1992 | Grobe |
| 5,117,981 A | 6/1992 | Crawford et al. |
| 5,144,942 A | 9/1992 | Decarie et al. |
| 5,178,282 A | 1/1993 | Williams |
| D341,159 S | 11/1993 | Watson et al. |
| 5,289,919 A * | 3/1994 | Fischer ...................... 206/571 |
| 5,311,990 A | 5/1994 | Kalinski |
| 5,315,985 A | 5/1994 | Decarie et al. |
| 5,318,543 A | 6/1994 | Ross et al. |
| 5,379,895 A | 1/1995 | Foslien |
| 5,392,918 A | 2/1995 | Harrison |
| 5,449,071 A * | 9/1995 | Levy .......................... 206/570 |
| 5,456,361 A | 10/1995 | Walsh et al. |
| 5,507,279 A | 4/1996 | Fortune et al. |
| D376,652 S | 12/1996 | Hunt et al. |
| 5,590,778 A * | 1/1997 | Dutchik ...................... 206/571 |
| 5,611,780 A | 3/1997 | Decarie et al. |
| 5,699,909 A | 12/1997 | Foster |
| 5,772,031 A * | 6/1998 | Landis ....................... 206/438 |
| 5,779,053 A | 7/1998 | Partika et al. |
| 5,848,700 A | 12/1998 | Horn |
| 5,947,284 A * | 9/1999 | Foster ........................ 206/364 |
| 5,947,296 A | 9/1999 | Castora |
| 6,012,586 A | 1/2000 | Misra |
| 6,036,021 A | 3/2000 | Moi |
| 6,039,183 A | 3/2000 | Rudnick et al. |
| 6,090,073 A | 7/2000 | Gill |
| 6,093,179 A | 7/2000 | O'Hara et al. |
| 6,112,900 A | 9/2000 | Adkins, Jr. |
| 6,116,426 A | 9/2000 | Slonim |
| D450,391 S | 11/2001 | Hunt et al. |

* cited by examiner

SURGICAL KIT FOR "PUSH" TYPE PERCUTANEOUS ENDOSCOPIC GASTROSTOMY PROCEDURES

BACKGROUND

The present invention relates to pre-packaged surgical kits in general, and more particularly to surgical kits for percutaneous endoscopic procedures.

Various medical procedures are simplified by providing the physician with a kit that contains the majority, if not all, of the necessary medical articles that the physician will need to complete a particular procedure. Kits may include articles such as, for example, drapes, syringes, scalpels, needles, clamps, gauze, sponges, drugs, sutures, and devices. Such kits are commonly provided for procedures such as, for example, percutaneous endoscopic gastrostomy ("PEG") and laparoscopic jejunostomy. These kits reduce the time spent by hospital personnel gathering the appropriate articles that are required for a particular procedure and ensure that the surgeon has each article at hand at the appropriate point in the procedure.

A PEG procedure is utilized to place a feeding tube into a patient that extends from the interior of the patient's stomach exteriorly of the patient. The feeding tube permits nutrients to be placed directly into a patient's stomach. This may be necessary when a patient has a disorder of the gastrointestinal tract, malabsorption (impaired absorption of nutrients, vitamins or minerals from the diet by the lining of the small intestine), or neurological or renal disorders. The feeding tube inserted using a PEG procedure is kept in place until a stoma is formed. Once a stoma is formed, the PEG feeding tube may be removed and replaced with an alternate feeding device.

While many current PEG surgical kits include the necessary medical implements or articles to complete a PEG procedure, the articles in such kits may not be arranged in the most effective and efficient manner within the kits.

Also, conventional PEG kits provide not only the surgical implements, such as scalpels, needles, scissors, and the like, but also "accessory" items such as swabs, gauze pads, single-use packages of ointments and lubricants, suture strands, sponges, and the like. These relatively small, loose, items are, however, relatively difficult to store in the kits. Such items may be simply placed loosely in the kit or provided in a sealed pouch. Once the kits or pouches are opened, these items tend to clutter the kit or are moved out of the kit to various locations by the surgical staff. It is difficult to maintain accountability of the items. Also, the accessory items are generally single-use disposable items and conventional kits do not provide a means for accountability and disposal of the devices after use.

SUMMARY

Objects and advantages of the invention will be set forth in part in the following description, or may be obvious from the description, or may be learned through practice of the invention.

The present invention provides a surgical kit for a PEG procedure, particulary a "push" type PEG procedure. The kit includes surgical articles and accessory items to be used in performing the PEG procedure.

An embodiment of a PEG surgical kit according to the invention includes a tray having a plurality of recesses formed therein for receiving surgical articles or implements useful in performing a particular surgical procedure. The terms surgical "articles" or "implements" are intended to encompass any combination of devices used in the PEG surgical procedure and may include, without limitation, scissors, clamps, forceps, medicines and drugs, syringes, needles, tubes, scalpels, snares, cannulas, and so forth. The kit also includes surgical articles that are particular to a "push" type PEG procedure, such as a "push" PEG tube, a bolus adapter assembly, locking ring, snare device, etc.

The kit may also include any combination of "accessory" surgical items. The term "accessory" item is meant to encompass generally loose ancillary articles such as any number of pre-packaged single-use disposable items. Such items may include, for example, sutures, swabs, ointment packages, lubricant packages, drapes, gauze pads, small vials or packages of drugs, and the like. In this regard, the kit according to the invention may include an accessory item container that may be received in a container recess defined in the tray. The accessory items may be placed in a separate container which is placed in the tray prior to sealing the tray.

The tray includes a cover that is sealed thereto, for example by an adhesive around a peripheral edge of the tray. In order to gain access to the contents of the tray, the cover is peeled or removed from the tray.

The tray includes a plurality of planar surfaces formed therein. The plurality of recesses are defined in the planar surfaces. The planar surfaces are offset vertically such that each planar surface is offset from at least one other planar surface and unobstructed access to certain of the recesses in at least one lower planar surface is obtained by removing at least one article from a recess in at least one upper planar surface. In particular embodiments, a first planar surface, a second planar surface and a third planar surface may be provided in the tray. The second planar surface may be offset from the first planar surface. The third planar surface may be offset from the first planar surface and/or the second planar surface.

A particular embodiment of a surgical kit according to the invention is a PEG kit wherein each recess is adapted to hold an article that is useful in performing a "push" type of percutaneous endoscopic gastrostomy procedure. At least one of the recesses may be adapted to retain at least a portion of a percutaneous endoscopic gastrostomy tube having an elongated tapered end configured for sliding the tube along a guide wire as the tube is pushed along the guide wire by the surgeon. In some embodiments, such a recess may be disposed on the second planar surface. A retrieval snare and/or a guide wire may be positioned over at least a portion of the percutaneous endoscopic gastrostomy tube. One of the recesses may be adapted to retain an exterior tube retention device, and such a recess may be disposed on the second planar surface in some embodiments. Another of the recesses may be adapted to retain an introducer cannula, and such a recess may be disposed in the third planar surface.

Some of the planar surfaces may have one or more bosses extending upwardly therefrom. In some embodiments, at least one boss may extend upwardly from the second planar surface. At least one boss may be disposed upon the first planar surface. An article may be positioned so that at least a portion of such an article is disposed about a boss.

The invention will be explained below in further detail by way of reference to an embodiment of the invention illustrated in the figures.

DETAILED DESCRIPTION

Reference will now be made in detail to embodiments of the invention, one or more examples of which are illustrated in the figures. The embodiments are provided by way of explanation of the invention, and not meant as a limitation of the invention. For example, features illustrated or described as part of one embodiment may be used with another embodiment to yield still a different embodiment. It is intended that the invention include these and other modifications as come within the scope and spirit of the invention.

An embodiment of a surgical kit according to the invention is illustrated in the figures as a percutaneous endoscopic gastrostomy ("PEG") kit 20. Such a PEG kit may be used in procedures that are characterized as "push-type" procedures. The PEG kit 20 may include a tray 22 having a plurality of planar surfaces and a plurality of recesses that may be disposed within the planar surfaces. The tray 22 may be formed of any suitable material, for example the tray 22 may be molded from a transparent or translucent substantially rigid plastic material (i.e., PETG). The tray 22 may have side walls 23 defining a depth of the tray 22.

As described in more detail below, the planar surfaces may be vertically offset (with reference to a horizontal surface upon which the tray rests) within the tray 22. For example, referring to FIGS. 1, 8, and 9, a plurality of substantially horizontal planar surfaces 64, 66, 68, and 70 are defined in the tray 22. The planar surfaces may be co-molded with the tray 22. Each of the planar surfaces is vertically offset within the tray 22 with respect to at least one other planar surface.

A plurality of recesses adapted to hold articles or implements that are useful in performing the "push" PEG procedure are defined in the various planar surfaces 64, 66, 68, and 70. Each recess may be adapted to hold one or more articles. Examples of recess configurations and respective articles held therein are discussed in greater detail below. The recesses may also include detents, protrusions, or the like to frictionally engage the articles and positively retain the articles within the respective recesses.

Figure 1:
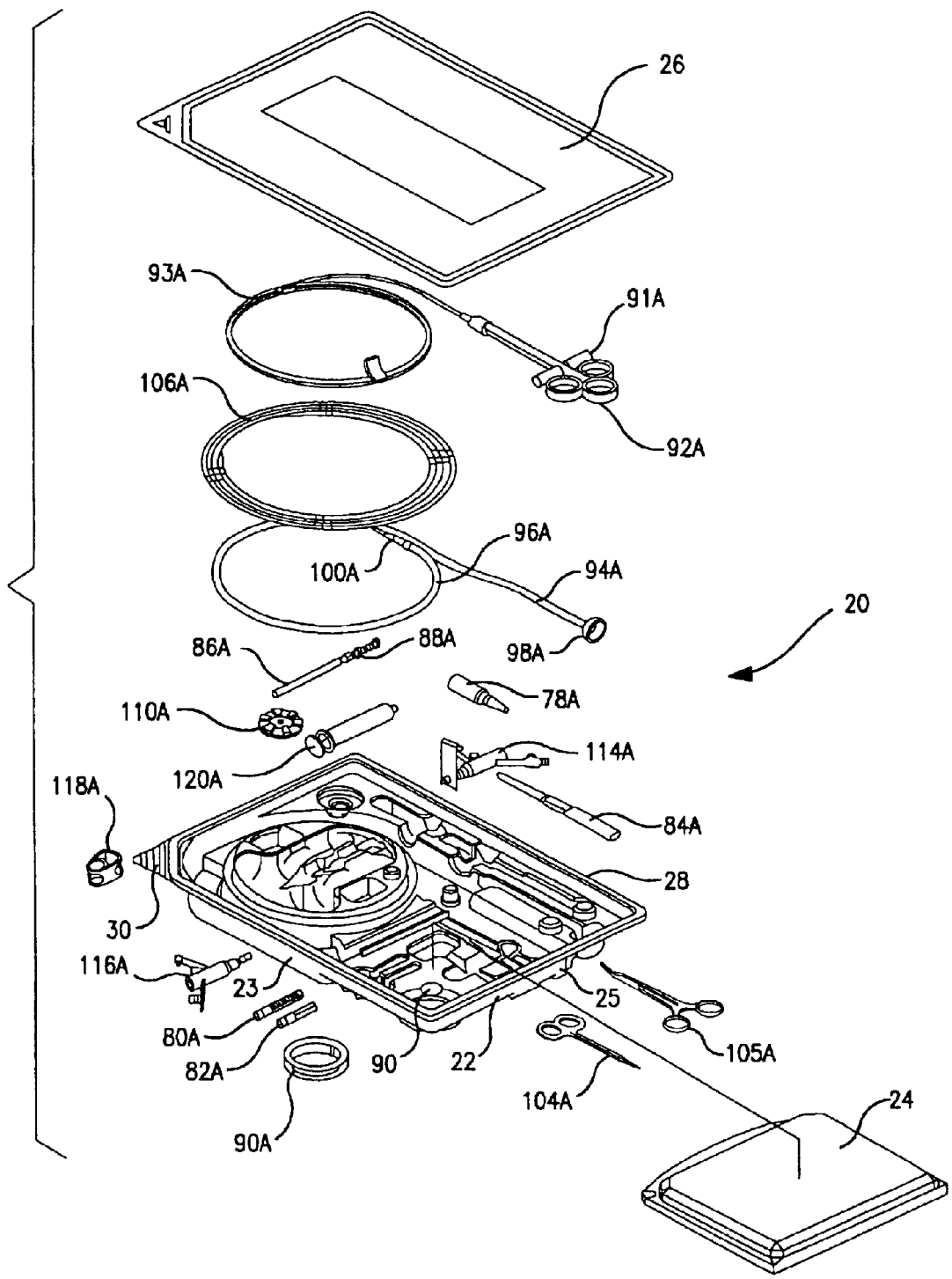
FIG. 1 is a perspective component view of a PEG surgical kit according to the present invention.

As seen in FIG. 1, a cover 26 may be positioned on the tray 22 and, in some embodiments, may be adhered to a relatively flat peripheral surface 28 of the tray 22. A corner 30 of the tray 22 may be configured so that a portion of the cover 26 is not adhered to the corner 30. In such an embodiment, a user may grasp the cover 26 that is positioned adjacent to the corner 30 to remove the cover 26 from the tray 22. The cover may be attached to the tray by any suitable method, including adhesives, heat sealing, sonic or thermal welding, solvents, etc. Once all of the articles have been placed into the tray 22 and the cover sealed to the tray, the kit is subjected to ETO (ethylene oxide) gas sterilization. For this reason, the cover 26 is gas permeable. A suitable cover material is Tyvek™, a spunbond polyolefin, from DuPont of Wilmington, Del. Any number of other permeable web materials suitable for ETO gas sterilization, such as Kraft paper, may be used as the cover 26.

As illustrated generally in the figures, a container 24 is provided with the kit 20. The container is desirably a substantially rigid structure adapted to fit at least partially within the tray 22. For example, the container 24 may rest upon the planar surface 64. Desirably, the container 24 is disposed generally at the top of the tray so that access is provided to the container 24 immediately upon removing the cover 26 from the tray 22. In this way, the container 24 can be the first item removed from the tray 22 without touching or displacing any of the other articles in the tray 22. The tray side walls 23 and a bumper wall 126 define a recess or nesting place for the container and engage or retain the container 24 in a precise location within the tray 22. In one embodiment, the container 24 may be press-fitted into the nesting place. In another embodiment, the container 24 may be loosely received into the nesting place.

FIGS. 3–6 illustrate an embodiment of a container 24 that may be used in the present invention. The container 24 may include a substantially rigid lid 34 and a base 36, the lid 24 and the base 36 being flexibly attached to each other by a hinge 38 (i.e., a living hinge) in a clam-shell configuration. In some embodiments, the lid 34 and the base 36 may not be attached to each other, or may be attached to each other using alternate configurations. The container may be molded or otherwise formed from the same polymer material as the tray 22. A lip 40 may be provided that extends around the edges of the lid 34 and the base 36. In particular embodiments, an extended portion 42 may be disposed along one edge of the lip 40 to enable a user to more easily open the container 24. One or both of the lips 40 may include a number of bosses 41 extending therefrom. These bosses 41 keep the opposing lips 40 spaced apart in a closed state of the container so that the ETO (ethylene oxide) sterilization gas can readily permeate into the container.

The container 24 is preferably configured to be reclosable. In this manner, the container 24 provides a convenient device for storing used articles prior to disposal. The container 24 may be variously configured so that it is reclosable, including, for example, providing a pair of bosses 44 disposed on the lid 34 that mate to a pair of detents 46 that are disposed on the base 36. Other mechanisms that may be useful to reclose the container 24 include adhesive, hook-and-loop fasteners, locking arms, and the like.

Figure 3:
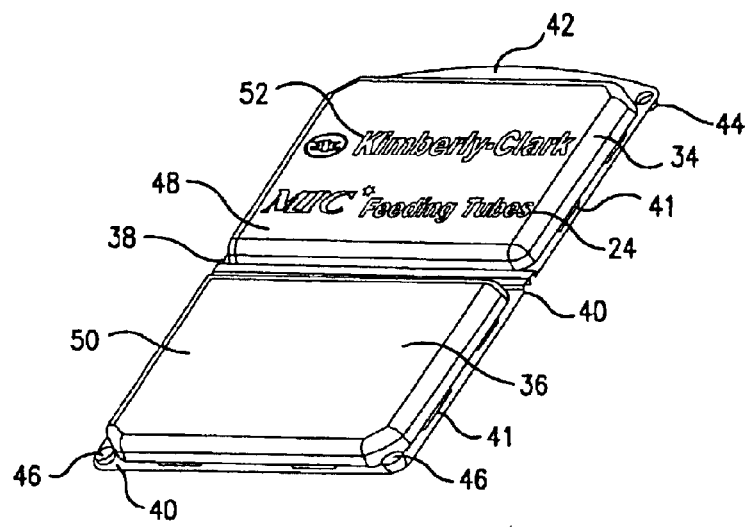
FIG. 3 is a perspective view of an embodiment of a container of the present invention.

Embossing, such as embossing 52 in FIG. 3, may be disposed on the outer surface 48 of the lid 34 or on the outer surface 50 of the base 36. Alphanumeric, numeric or other characters may be embossed on the container 24.

The tray 22 and container 24 are illustrated as generally rectangular in the figures. However, it should be appreciated that these components may take on any convenient shape.

Figure 6:
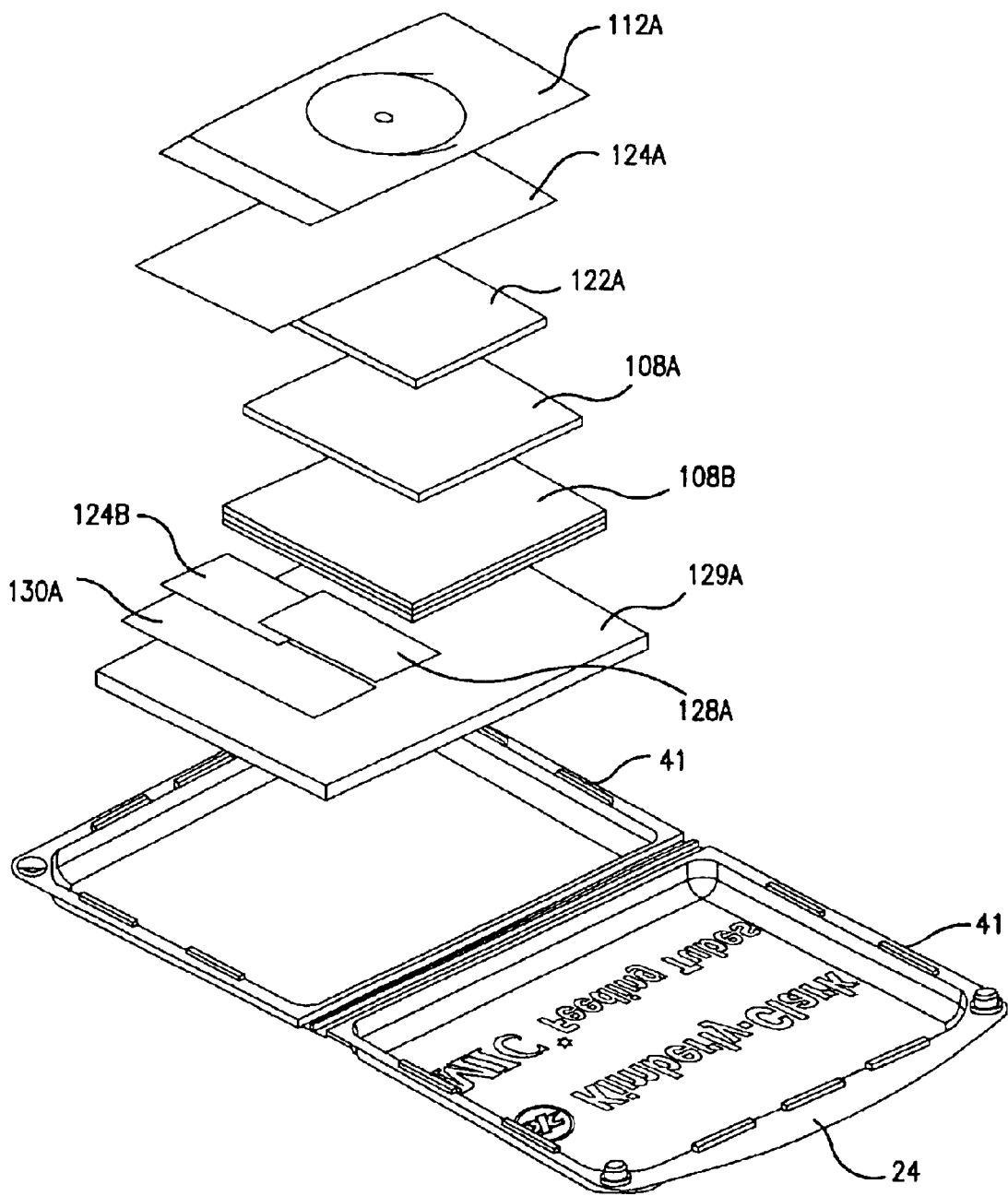
FIG. 6 is a perspective component view of an embodiment of the container according to the invention having been removed from the tray.

Referring to FIG. 6, the container 24 may be adapted to hold a variety of accessory medical articles including, for example, suture strands (packaged) 112A, swabs (i.e., povidone-iodine prep swabsticks) 124A, lidocaine insert 122A, fenestrated gauze pads 108A, gauze pads 108B, fenestrated drape 129A, single-use packages of lubricant 130A, single-use packages of ointment 124B (i.e., povidone-iodine ointment), antibiotic ointment 128A, sponges, and the like. As described, the container is particularly well suited for retaining these devices after they have been used for later disposal.

As shown in the Figures in general, the tray 22 may include a first planar surface 64. Several recesses are disposed in surface 64, including two recesses 76 that may be used to hold or support coiled articles and a needle recess 81. The recesses 76 can be seen particularly in FIGS. 8 and 9 and may be, for example, generally circumferentially extending recesses that extend around at least a portion of a generally circular structure that defines planar surface 68, as described in greater detail below. The needle recess 81 may include two elongated recesses 80 and 82 so that the needle recess 81 may hold two needles securely. In selected embodiments, recess 80 may be configured to hold a filter needle 80A and the recess 82 may be configured to hold a needle 82A. A recess 90 may be disposed in the first surface 64. This recess would hold a looped placement wire 90A wound on a spool if the kit were configured particularly for a "pull" PEG procedure. The wire 90A is not necessary for the "push" procedure, as described below. However, from a manufacturing cost standpoint, it is more economical to mold the same tray 22 for both procedures. Thus, the tray 22 configured for a "push" procedure may contain an article recess that is empty.

The first surface 64 may also include a recess 103 that may be configured to have elongated portions 104 and 105. A pair of surgical scissors 104A may be disposed in the portion 104 of the recess 103, and a hemostat 105A may be disposed in the portion 105 of the recess 103.

Figure 2:
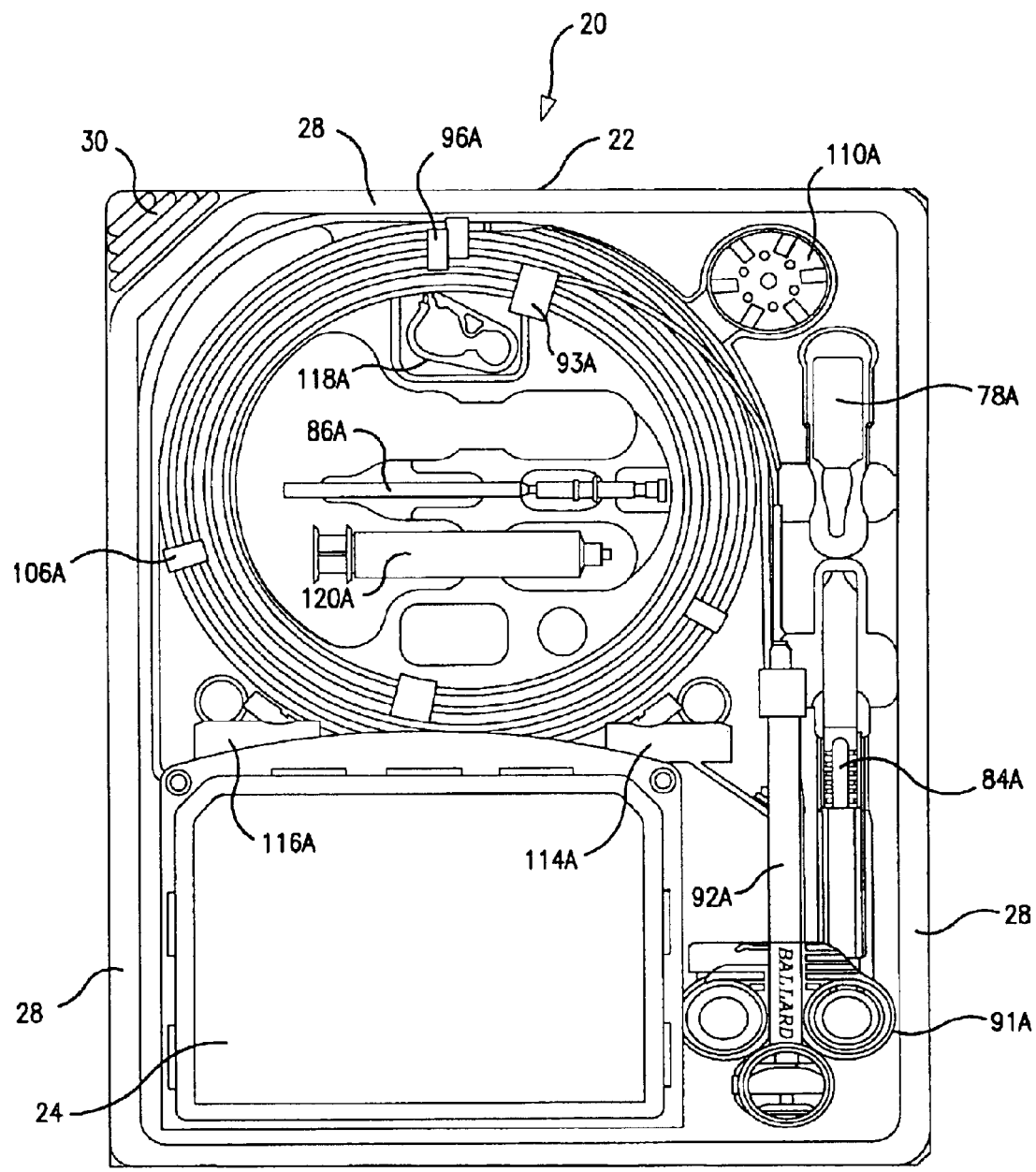
FIG. 2 is a top plan view of the embodiment shown in FIG. 1.

The first surface 64 may also include a recess 115 that may be elongated and have two spaced apart ends 114 and 116. As shown in FIGS. 1 and 2, a bolus feeding adapter 114A may be at least partially disposed in the end 114 of the recess 115. A universal feeding adapter 116A may also be at least partially disposed in the end 116 of the recess 115.

The first planar surface in the illustrated embodiment also defines a nesting place for the container 24. An elongated boss 126 may be disposed on the first planar surface 64 for this purpose. This boss 126 and two of the tray side walls 23 cooperate to define a recess or storage location for the container 24 on the first planar surface 64. The container 24 actually rests on the surface 64 above a number of the article recesses. For example, referring to FIGS. 1, 8, and 9 the recesses 80, 81, 82, 90, 103, 104, and 105, as well as their associated articles, are all disposed under the container 24. The physician must first remove the container 24 to gain access to these recesses.

Figure 7:
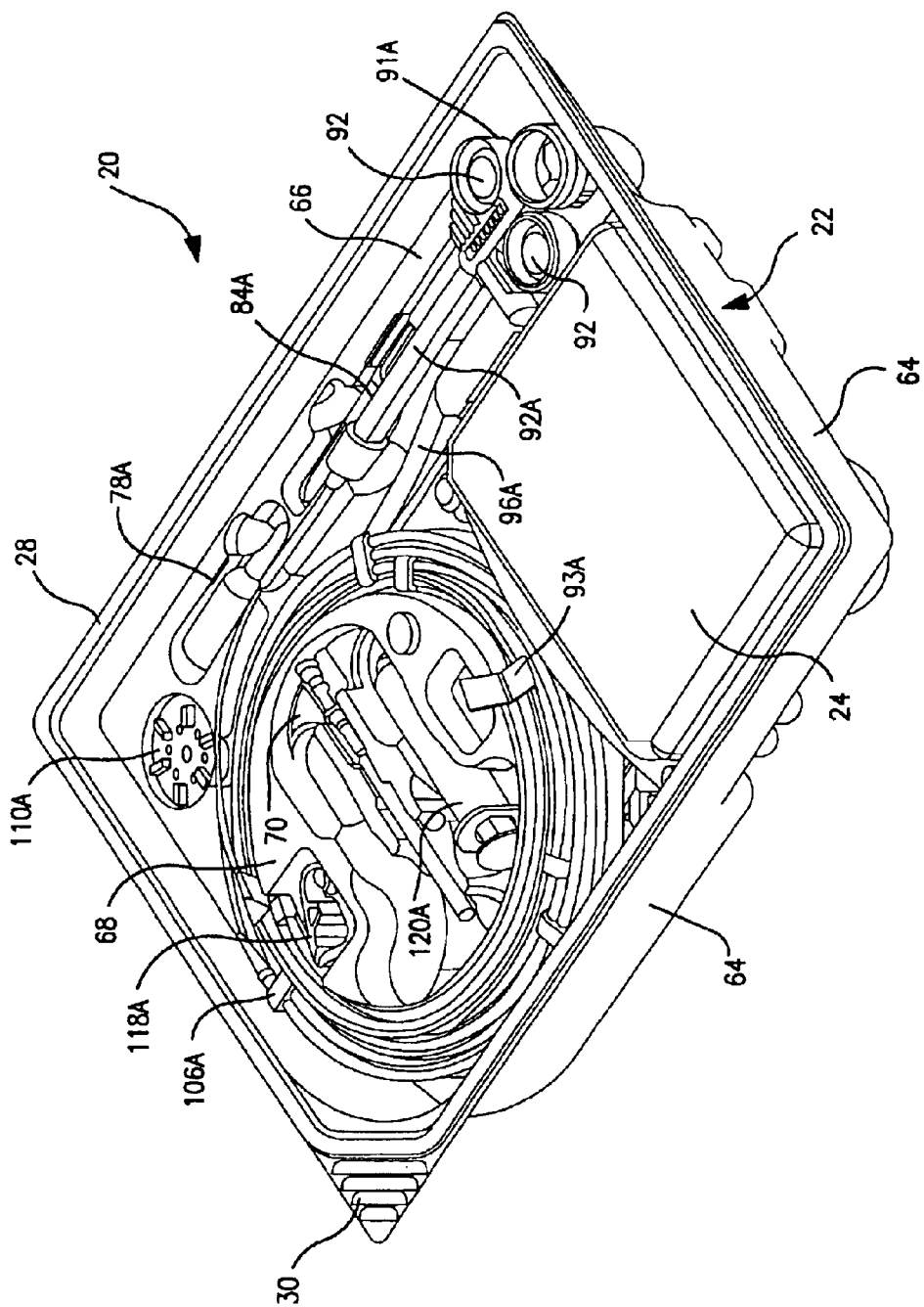
FIG. 7 is a perspective view of the tray and stored components, including the container.
Figure 8:
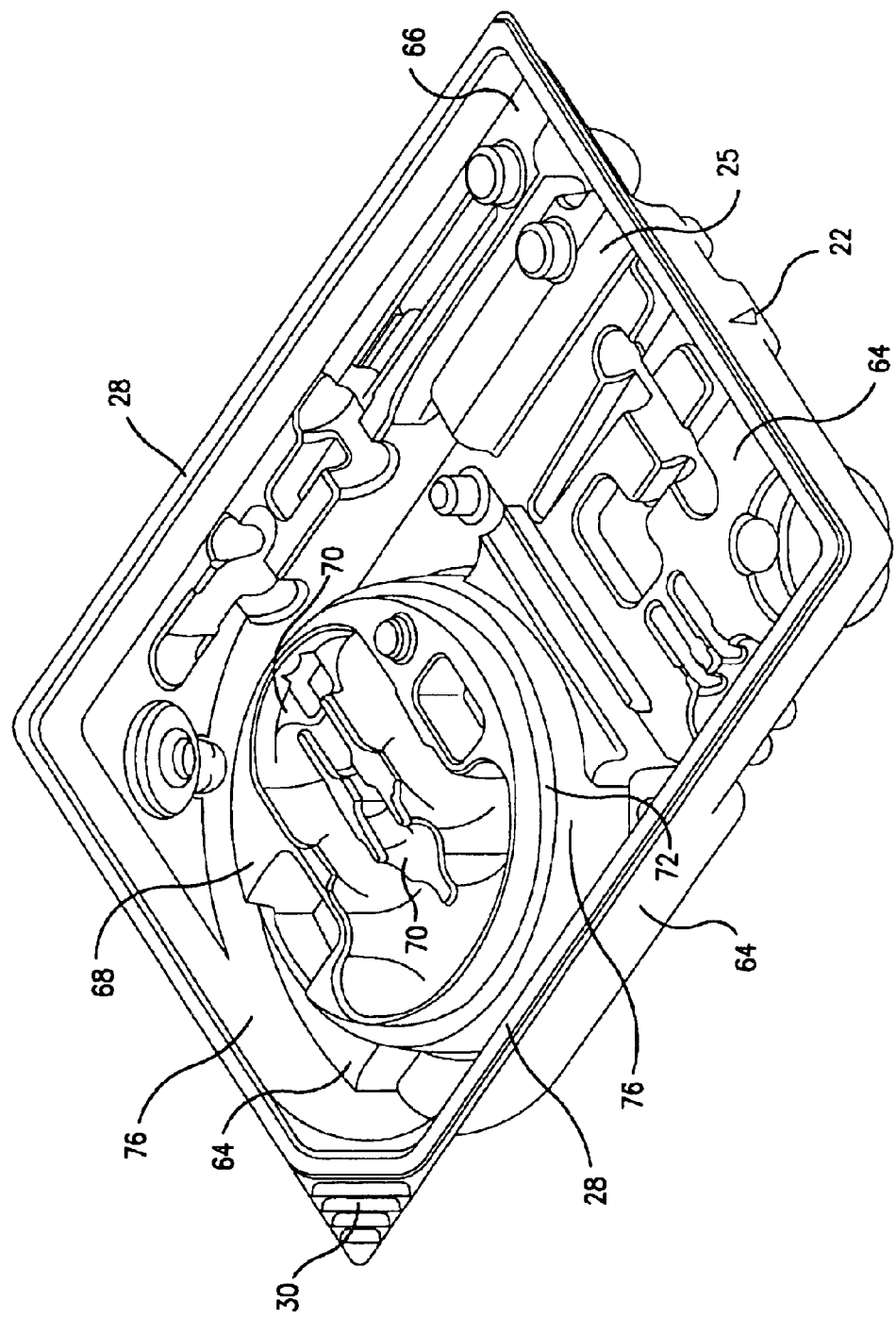
FIG. 8 is a perspective view of an empty tray particularly illustrating the various structural features of the tray.
Figure 9:
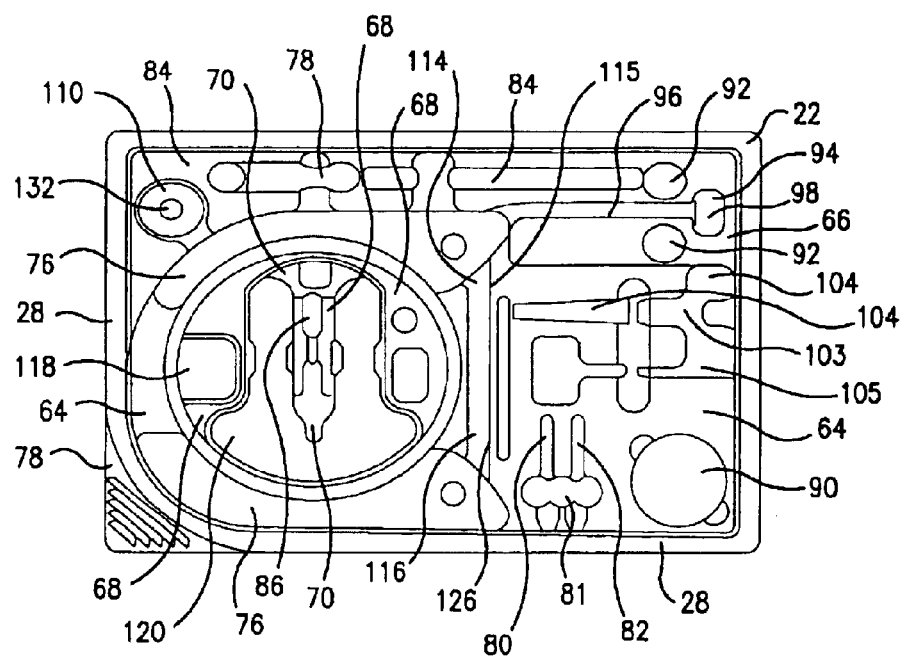
FIG. 9 is a top plan view of the tray shown in FIG. 8.
Figure 10:
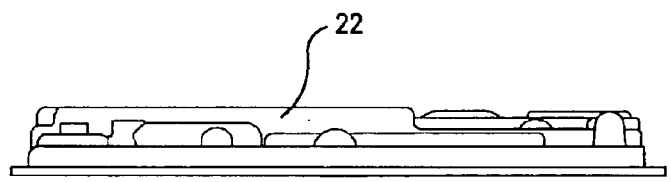
FIG. 10 is a side view of tray shown in FIG. 9 with the bottom surface of the tray facing upwards.
Figure 11:
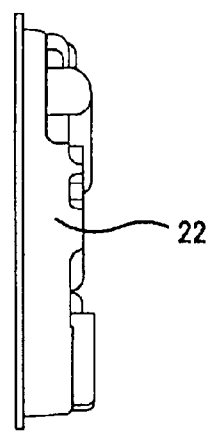
FIG. 11 is an end view of the tray shown in FIG. 9 with the bottom surface of the tray facing towards the right.

As seen in FIGS. 7–9, a second planar surface 66 may also be provided and may, in selected embodiments, be offset from the first planar surface 64. Numerous recesses may be disposed in the second planar surface 66 including a recess 78 that is adapted to hold a container of lidocaine 78A and a recess 84 that may be adapted to hold a scalpel 84A, as shown in FIG. 7.

A recess 110 may also be provided in the second planar surface 66, the recess 110 being adapted to hold an exterior tube retention device 110A. In some embodiments, a SECUR-LOK™ ring, available from Ballard Medical Products in Draper, Utah, may be used as an exterior tube retention device 110A. A boss 132 may be disposed in the recess 110 to support the exterior tube retention device 110A.

The second planar surface 66 may also include a recess 94 that is adapted to hold at least a portion of a percutaneous endoscopic gastrostomy (PEG) tube 94A that is suitable for use in a "push" procedure, as seen in FIG. 1. Such a PEG tube typically includes an internal retention device such as a bumper 98A, an elongated tube 96A, and an elongated tapered tip 100A. The recess 94 may include a rounded portion 98 that will hold the bumper 98A. The recess 94 may also include an elongated portion 96 that will hold at least a portion of the elongated tube 96A. The portion of the elongated tube 96A that is not disposed in the elongated portion 96 of the recess 94 may be coiled and placed within the recesses 76 that are formed in the first planar surface 64. In such an embodiment, a portion of the coiled elongated tube 96A may rest on the portions of the first planar surface 64 that are disposed between the recesses 76.

For "push" type PEG procedures, a coiled sheathed guide wire 106A is provided in the kit, as seen in FIGS. 1, 2, and 7. The guide wire 106A may be placed in the recess 76 on top of the coiled end of the snare 93A and coiled tube 96A of the PEG tube 94A.

Figures 4, 5:
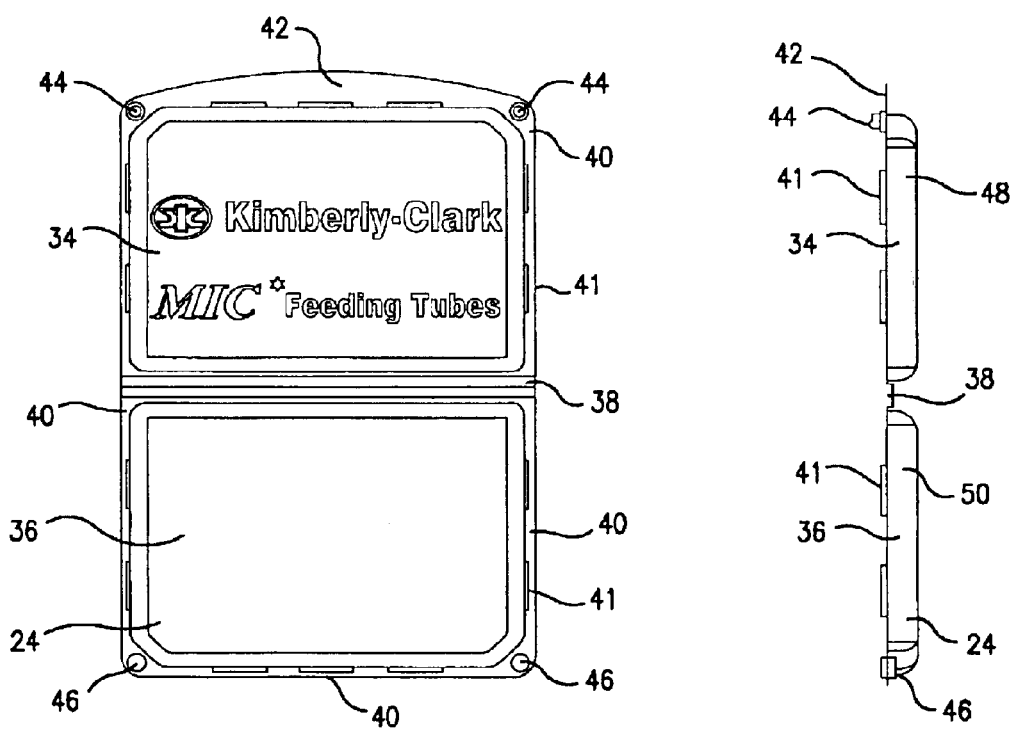
FIG. 4 is a bottom view of the container shown in FIG. 3.
FIG. 5 is a side view of the container shown in FIG. 3.

One or more bosses 92 may be disposed on the second planar surface proximate to the recess 94, one boss 92 being disposed on one side of the recess 94 and another boss 92 being disposed on the other side of the recess 94. In such an embodiment, a retrieval snare 92A, as seen in FIG. 4, may be positioned on the second planar surface so that the handle 91A of the retrieval snare 92A is secured in place by the bosses 92. In such an embodiment, the retrieval snare 92A is positioned over the PEG tube 94A, the bumper 98A being disposed under the handle 91A of the retrieval snare 92A. The coiled end 93A of the retrieval snare 92A may be disposed over the coiled tube 96A of the PEG tube 94A so that both coils 93A and 96A supported by the first planar surface 64 and may be at least partially disposed in the recesses 76.

A third planar surface 68 may also be provided in the tray 22. The third planar surface may be offset from the first planar surface 64, from the second planar surface 66, or from both the first and second planar surfaces 64 and 66, respectively. In the embodiment depicted in the Figures, the third planar surface 68 may be disposed within the interior of the coils 93A and 96A. A recess 120 may be formed in the third planar surface as shown in FIG. 9. The recess 120 may be configured to hold one or two twelve-ounce syringes 120A. A recess 118 may also be disposed in the third planar surface 68 and may be adapted to hold a tubing clamp 118A.

A fourth planar surface 70 may be disposed adjacent to the third planar surface 68, as seen in FIGS. 8 and 9. A recess 86 that is adapted to hold an introducer cannula 86A may be formed in the third and fourth planar surfaces 68 and 70, respectively.

In selected embodiments and as shown in FIG. 9, a fifth planar surface 72 may be provided that is adjacent to the fourth planar surface 70. The fifth planar surface 72 may be configured to provide additional support to the coils 93A and 96A.

The tray 22 may also be configured to hold a pamphlet (not shown) that may contain various information such as, for example, directions for using the PEG kit 20.

Description of a "Push-Type" PEG Procedure

The kit 20 of the present invention is suitable for use with a "push" type percutaneous endoscopic gastrostomy procedure. In such a procedure, a patient is sedated and an endoscope is passed down the throat of the patient until the end of the endoscope is positioned in the stomach of the patient. With the patient in the supine position, the stomach is insufflated with air.

The kit 20 may be opened by removing the cover 26. The container 24 is removed from the kit 20 and opened. The gastrostomy site is selected and the skin is prepared and draped at the insertion site. Medical articles such as povidone-iodine ointment and swabsticks and a surgical drape contained within the container 24 are used for this purpose. A local anesthesia such as, for example, lidocaine 78A, is given. Needles such as the filter needle 80A may be used to administer the anesthesia.

A small incision is made through the skin using a scalpel such as the scalpel 84A. An introducer cannula such as the introducer cannula 86A having an internal piercing stylet 88A is inserted through the incision and advanced through the peritoneum and the stomach wall. When the introducer cannula 86A is observed in the stomach, the internal piercing stylet 88A is removed, leaving the blunt-end cannula 86A within the stomach.

In the "push" version of a PEG procedure, a guide wire 106A is fed through the introducer cannula 86A (after the internal piercing stylet 88A is removed) and into the patient's stomach. A retrieval snare such as retrieval snare 92A is inserted down the endoscope, and the guide wire 106A is grasped with the snare. The retrieval snare 92A and guide wire 106A are then drawn through the endoscope.

The endoscope and the guide wire 106A are removed through the oropharynx. The guide wire 106A is fed into the cannula 86A as the endoscope is retracted. One end of the guide wire 106A is pulled out of the mouth of the patient, and the other end of the guide wire 106A remains positioned outside of the abdomen of the patient. The introducer cannula 86A is kept in place in the stomach.

The tapered tip 100A of the PEG tube 94A is then slid over the end of the guide wire 106A that is protruding from the mouth of the patient. The PEG tube 94A may be lubricated with a water-soluble jelly for this purpose. The PEG tube 94A is pushed over the guide wire 106A through the oropharynx, esophagus, and into the stomach. The cannula 86A is removed from the incision site and the tapered tip 100A of the PEG tube 94A is pushed through the incision in the abdominal wall until the internal bumper 98A on the opposite end of the PEG tube 94A rests against the interior of the abdominal wall.

A sterile gauze dressing may then be applied to the site. A section of the PEG tube 94A, including the loop 102A is severed from the PEG tube 94A and discarded. An exterior tube retention device such as the retention device 110A is positioned on the exterior portion of the PEG tube 94A to prevent the PEG tube 94A from slipping back through the incision. For example, a SECUR-LOK™ ring, available from Ballad Medical Products in Draper, Utah, may be slid over the exposed end of the PEG tube 94A and pushed until the SECUR-LOK™ ring is adjacent to the gauze dressing. A piece of suture may be tied around the neck of the SECUR-LOK™ ring to prevent it from slipping while the stoma is healing. The PEG tube 94A may then be cut and an appropriate feeding adaptor, such as, for example, the bolus feeding adaptor 114A or the universal feeding adaptor 116A, may be attached to the PEG tube 94A.

From the foregoing description, it should be appreciated that the arrangement of the vertically offset planar surfaces and their respective article recesses results in an arrangement wherein certain of the articles may be removed from the kit before unobstructed access is provided to certain underlying articles. The articles are arranged so that, desirably, such articles may be readily removed from the tray in their order of use. For example, in the embodiment illustrated in the Figures wherein the surgical kit is a PEG kit, the container 24 contains many of accessory items needed to prep the surgical site on the patient. The container is seated in its recess on the first planar surface 64 and is readily removable upon removing the cover 26 from the tray 22. The snare device 92A within recess 92 is used before the PEG tube 94A within recess 94, and the snare device 92A must be removed before the PEG tube 94A can be removed. The feeding adapters 114A and 116A within respective recesses 114 and 116 are used towards the end of a PEG procedure. Access to the adapters is provided after removal of the snare 92A and PEG tube 94A.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A kit adapted to be utilized in a "push" percutaneous endoscopic gastrostomy (PEG) procedure comprising:

a tray, said tray further comprising a plurality of planar surfaces, wherein at least three of the planar surfaces have at least one recess disposed therein and holding at least one article used in performing a "push" PEG procedure; and a container adapted to fit at least partially within the tray, the container adapted to rest upon at least one of the plurality of planar surfaces that has at least one recess disposed therein, wherein the planar surface onto which the container rests is outside of the perimeter defined by at least two of the other planar surfaces, the container adapted to be reclosable and having a lid and a base that define an interior space when the container is in the closed position and wherein at least two different types of accessory articles used in performing the "push" PEG procedure are retained in the interior space such that the container completely surrounds the accessory articles; and wherein said planar surfaces are offset vertically and said recesses positioned within said tray such that articles in at least one upper said planar surface must be removed from said tray prior to access being provided to articles in at least one lower said planar surface, said articles correspondingly arranged in said tray such that access is provided to said articles in their order of use for the "push" PEG procedure.

2. The kit as in claim 1, further comprising a cover sealed to at least a portion of said tray.

3. The kit as in claim 2, wherein said cover is formed from a permeable web.

4. The kit as in claim 1, wherein at least one of said recesses contains at least a portion of a percutaneous endoscopic gastrostomy tube.

5. The kit as in claim 1, wherein at least one of said recesses contains a feeding tube retention device received therein.

6. The kit as in claim 1, wherein said tray comprises a container recess disposed above a first said planar surface such that at least a portion of said container rests on said first planar surface, and further comprising at least one said recess defined in said first planar surface below said container.

7. The kit as in claim 1, further comprising at least one boss member extending upwardly from one of said planar surfaces, said boss member extending through at least a portion of one of said articles.

8. A kit adapted to be utilized in a "push" percutaneous endoscopic gastrostomy (PEG) procedure comprising:
   a tray, said tray further comprising a plurality of planar surfaces and at least one recess disposed in at least one of the planar surfaces, each recess adapted to hold at least one article used in performing a "push" PEG procedure;
   a container adapted to fit at least partially within the tray, the container adapted to rest upon at least one of the plurality of planar surfaces, the container adapted to be reclosable and to retain at east one accessory article used in performing the "push" PEG procedure;
   wherein said planar surfaces are offset vertically and said recesses positioned within said tray such that articles in at least one upper said planar surface must be removed from said tray prior to access being provided to articles in at least one lower said planar surface, said articles correspondingly arranged in said tray such that access is provided to said articles in their order of use for the "push" PEG procedure,
   wherein at least one of said recesses contains at least a portion of a percutaneous endoscopic gastrostomy tube; and
   a retrieval snare disposed in a retrieval snare recess defined in one of said planar surfaces such that said retrieval snare is positioned over at least a portion of said percutaneous endoscopic gastrostomy tube.

9. A kit adapted to be utilized in a "push" percutaneous endoscopic gastrostomy (PEG) procedure comprising:
   a tray, said tray further comprising a plurality of planar surfaces and at least one recess disposed in at least one of the planar surfaces, each recess adapted to hold at least one article used in performing a "push" PEG procedure; and
   a container adapted to fit at least partially within the tray, the container adapted to rest upon at least one of the plurality of planar surfaces, the container adapted to be reclosable and to retain at least one accessory article used in performing the "push" PEG procedure;
   wherein said planar surfaces are offset vertically and said recesses positioned within said tray such that articles in at least one upper said planar surface must be removed from said tray prior to access being provided to articles in at least one lower said planar surface, said articles correspondingly arranged in said tray such that access is provided to said articles in their order of use for the "push" PEG procedure;
   wherein at least one of said recesses contains at least a portion of a percutaneous endoscopic gastrostomy tube, and further comprising a coiled guide wire disposed above said portion of said percutaneous endoscopic gastrostomy tube.

10. The kit as in claim 9, wherein said coiled guide is disposed in the same respective said recess as said portion of said percutaneous endoscopic gastrostomy tube such that said coiled guide wire must be removed from said tray prior to providing access to said percutaneous endoscopic gastrostomy tube.

11. A kit adapted to be utilized in a "push" percutaneous endoscopic gastrostomy (PEG) procedure comprising:
   a tray, said tray further comprising a plurality of planar surfaces and at least one recess disposed in at least one of the planar surfaces, each recess adapted to hold at least one article used in performing a "push" PEG procedure; and
   a container adapted to fit at least partially within the tray, the container adapted to rest upon at least one of the plurality of planar surfaces, the container adapted to be reclosable and having a lid and a base that define an interior space when the container is in the closed position and wherein at least one accessory article used in performing the "push" PEG procedure is retained in the interior space;
   wherein said planar surfaces are offset vertically and said recesses positioned within said tray such that articles in at least one upper said planar surface must be removed from said tray prior to access being provided to articles in at least one lower said planar surface, said articles correspondingly arranged in said tray such that access is provided to said articles in their order of use for the "push" PEG procedure;
   at least one boss member extending upwardly from one of said planar surfaces, said boss member extending through at least a portion of one of said articles; and
   wherein said boss member extends through a handle portion of a snare device.

12. A surgical kit for use in performing a percutaneous endoscopic gastrostomy (PEG) "push" type procedure, comprising:
   a tray, said tray further comprising
   a first planar surface comprising at least one first planar recess disposed therein;
   a second planar surface comprising at least one second planar recess disposed therein, said second planar surface being vertically displaced from said first planar surface;
   a third planar surface comprising at least one third planar recess disposed therein, said third planar surface being vertically displaced from said first planar surface and said second planar surface;
   a removable container disposed within said tray, said container seated at least in part upon at least one of the plurality of planar surfaces, the container adapted to be reclosable and to retain additional articles useful in performing the PEG procedure;
   a cover sealed over said tray; and
   wherein each said recess contains at least one article useful in performing the "push" type PEG procedure, at least one of said articles being a PEG tube having an elongated tapered end for use in the "push" PEG procedure.

13. The kit as in claim 12, wherein at least one recess disposed in said second planar surface contains at least a portion of said PEG tube.

14. The kit as in claim 13, wherein said PEG tube comprises a bumper, said bumper disposed within at least one recess in said second planar surface.

15. The kit as in claim 12, wherein at least one recess disposed in sa third planar surface contains an introducer cannula.

16. The kit as in claim 12, wherein said cover is formed of a permeable web.

17. The kit as in claim 12, wherein at least one of said recesses disposed in said second planar surface contains an exterior tube retention device.

18. The kit as in claim 12, wherein said container rests on at least a portion of said first planar surface.

19. The kit as in claim 12, further comprising at least one boss extending upwardly from one of said planar surfaces and engaging one of said articles.

20. A surgical kit for use in performing a percutaneous endoscopic gastrostomy (PEG) "push" type procedure, comprising:

a tray, said tray further comprising a first planar surface comprising at least one first planar recess disposed therein;

a second planar surface comprising at least one second planar recess disposed therein, said second planar surface being vertically displaced from said first planar surface;

a third planar surface comprising at least one third planar recess disposed therein, said third planar surface being vertically displaced from said first planar surface;

a removable container disposed within said tray, said container seated at least in part upon at least one of the plurality of planar surfaces, the container adapted to be reclosable and to retain additional articles useful in performing the PEG procedure;

a cover sealed over said tray;

wherein each said recess contains at least one article useful in performing the "push" type PEG procedure, at least one of said articles being a PEG tube having an elongated tapered end for use in the "push" PEG procedure; and wherein at least one recess disposed in said first planar surface contains a guide wire over which said PEG tube is pushed in the PEG procedure.

21. A surgical kit for use in performing a percutaneous endoscopic gastrostomy (PEG) "push" type procedure, comprising:

a tray, said tray further comprising a first planar surface comprising at least one first planar recess disposed therein;

a second planar surface comprising at least one second planar recess disposed therein, said second planar surface being vertically displaced from said first planar surface;

a third planar surface comprising at least one third planar recess disposed therein, said third planar surface being vertically displaced from said first planar surface;

a removable container disposed within said tray, said container seated at least in part upon at least one of the plurality of planar surfaces, the container adapted to be reclosable and to retain additional articles useful in performing the PEG procedure;

a cover sealed over said tray; and wherein each said recess contains at least one article useful in performing the "push" type PEG procedure, at least one of said articles being a PEG tube having an elongated tapered end for use in the "push" PEG procedure; and at least one boss extending upwardly from one of said planar surfaces and engaging one of said articles;

wherein said boss extends from said second planar surface and extends through a handle portion of a snare device.

* * * * *